(12) United States Patent
Marchetti et al.

(10) Patent No.: US 11,857,529 B2
(45) Date of Patent: Jan. 2, 2024

(54) METHODS FOR TREATING MELANOMA

(71) Applicant: Olatec Therageutics, Inc., New York, NY (US)

(72) Inventors: Carlo Marchetti, Denver, CO (US); Charles A. Dinarello, Boulder, CO (US)

(73) Assignee: OLATEC THERAPEUTICS, INC., New York, NY (US)

( * ) Notice: Subject to any disclaimer, the term of this patent is extended or adjusted under 35 U.S.C. 154(b) by 668 days.

(21) Appl. No.: 17/021,733

(22) Filed: Sep. 15, 2020

(65) Prior Publication Data

US 2020/0405681 A1 Dec. 31, 2020

Related U.S. Application Data

(63) Continuation of application No. PCT/US2019/022770, filed on Mar. 18, 2019.

(60) Provisional application No. 62/645,999, filed on Mar. 21, 2018.

(51) Int. Cl.
*A61K 31/275* (2006.01)
*A61P 35/00* (2006.01)
*C07K 16/28* (2006.01)
*A61K 9/00* (2006.01)

(52) U.S. Cl.
CPC ............ *A61K 31/275* (2013.01); *A61P 35/00* (2018.01); *C07K 16/2818* (2013.01); *A61K 9/0053* (2013.01)

(58) Field of Classification Search
CPC .................................................... A61K 31/275
See application file for complete search history.

(56) References Cited

U.S. PATENT DOCUMENTS

| 8,476,316 | B2 * | 7/2013 | St. Laurent | A61K 31/275 |
| | | | | 514/708 |
| 10,548,870 | B2 * | 2/2020 | Dinarello | A61P 31/00 |
| 11,517,554 | B2 * | 12/2022 | Dinarello | A61K 9/0053 |
| 11,576,888 | B2 * | 2/2023 | Marchetti | A61K 31/275 |
| 2016/0362489 | A1 | 12/2016 | Yang | |

FOREIGN PATENT DOCUMENTS

| WO | 2016131098 A1 | 8/2016 |
| WO | 2017184746 A1 | 10/2017 |
| WO | 2018204764 A1 | 11/2018 |

OTHER PUBLICATIONS

Extended European Search Report dated Oct. 19, 2021 for European Application No. 19771591.5. 1 page.
Ahmad, I. et al "Thymoquinone suppresses metastasis of melanoma cells by inhibition of NLRP3 inflammasome", Toxicology and Applied Pharmacology, 2013, vol. 270, No. 1; pp. 70-76.
Da Silva, Wanessa Cardoso, et al., "Data on inflammasome gene polymorphisms of patients with sporadic malignant melanoma in a Brazilian cohort", Data in Brief, Nov. 24, 2016 (Nov. 24, 2016), vol. 10. pp. 33-37.
Hu, Hao , et al., "Long non-coding RNA XLOC_000647 suppresses progression of pancreatic cancer and decreases epithelial-mesenchymal transition-induced cell invasion by down-regulating NLRP3", Molecular Cancer, Jan. 31, 2018 (Jan. 31, 2018), vol. 17, Iss. 18, pp. 1-14. Entire document, pp. 1-14.
Kopalli, Spandana R., et al., "NLRP3 Inflammasome Activation Inhibitors in Inflammation-Associated Cancer Immunotherapy: An Update on the Recent Patents", 2018, 13, 106-117.
Marchetti, Carlo , et al., "OLT1177, a β-sulfonyl nitrile compound, safe in humans, inhibits the NLRP3 inflammasome and reverses the metabolic cost of inflammation", Proceedings of the National Academy of Sciences of the United States of America, Jan. 29, 2018 (Jan. 29, 2018), vol. 115, No. 7, pp. E1530-E1539.
Voigt, Cornelia , et al., "Cancer cells induce interleukin-22 production from memory CD4+ T cells via interleukin-1 to promote tumor growth", vol. 114, No. 49, Dec. 5, 2017.
Yao, Yikun , et al., "Antigen-specific Cdb+ T cell feedback activates N-LRP3 inflammasome in antigen-presenting cells through perforin", Nature Communications, May 24, 2017 (May 24, 2017), vol. 8, No. 15402, pp. 1-17.
Zhu, Zhaowei , et al., "Targeting the inflammatory pathways to enhance chemotherapy of cancer", pp. 95-105, Jul. 15, 2011.
International Search Report dated Jun. 27, 2019 cited in PCT/US2019/022770.

\* cited by examiner

*Primary Examiner* — Golam M Shameem
(74) *Attorney, Agent, or Firm* — Perkins Coie LLP; Viola Kung

(57) ABSTRACT

The present invention is directed to a method for preventing and/or treating melanoma such as superficial spreading melanoma, nodular melanoma, lentigo maligna melanoma, and acral lentiginous melanoma. The method comprises administering to a subject in need thereof an effective amount of dapansutrile. The method optionally comprising co-administering anti-PD-1 antibody with dapansutrile. A preferred route of administration is oral administration.

6 Claims, 10 Drawing Sheets

METHODS FOR TREATING MELANOMA

This application is a continuation of PCT/US2019/022770, filed Mar. 18, 2019; which claims the benefit of U.S. Provisional Application No. 62/645,999, filed Mar. 21, 2018. The contents of the above-identified applications are incorporated herein by reference in their entirety.

FIELD OF THE INVENTION

The present invention relates to methods for treating melanoma by administering an effective amount of dapansutrile.

BACKGROUND OF THE INVENTION

Tumorigenesis is initiated by genomic alterations including point mutations, gene deletion, chromosomal rearrangements leading to cell transformation, self-sufficient proliferation, insensitivity to anti-proliferative signals, evasion of apoptosis and unlimited replicative potential, leading ultimately to tissue invasion and metastasis. However, expansion of tumor cells is linked to a complex network of events that involve both cancer and non-cancer cells. Chronic inflammation is a classic example of such promoting conditions (1, 2).

The pro-inflammatory cytokine IL-1β is a potent mediator of many chronic inflammatory diseases (3). Consistent with the linkage of cancer to chronic inflammation, it has been shown that IL-1β is over-expressed in several tumors and functions as an inducer of tumor promoting mechanisms including angiogenesis, immunosuppression, recruitment of tumor-associated macrophages (TAMs) and metastasis (4-6).

Melanoma develops when unrepaired deoxyribonucleic acid ("DNA") damage to skin cells triggers mutations which cause skin cells to proliferate, ultimately forming malignant tumors. These tumors originate in melanocytes, which are located within the basal layer of the epidermis. Melanomas are often caused by ultraviolet (UV) exposure and is the cause-of-death for more than 70,000 people in the United States, per year.

There are four types of melanomas: superficial spreading melanoma, lentigo maligna melanoma, acral lentiginous melanoma, and nodular melanoma. Superficial spreading melanoma is the most common and grows along the top layer of the skin before penetrating more deeply into the skin. Lentigo maligna melanoma is similar to the superficial spreading melanoma and occurs most often in the elderly, arising on chronically sun-exposed, damaged skin. Acral lentiginous melanoma also spreads superficially before penetrating more deeply and tends to advance into malignancy more frequently than superficial spreading melanoma and lentigo maligna melanoma. Nodular melanoma is most often invasive when first diagnosed.

Melanomas are classified in stages, which refer to the thickness, depth of penetration, and the degree to which the melanoma has spread. Early melanomas (stages 0 and I) are generally localized. Stage 0 tumors are generally non-invasive and often have not penetrated below the epidermis. Stage I tumors have often invaded into the dermis, are small, and are a low risk for metastasis. Stage II tumors are localized, larger, and are at a high risk for metastasis. Once the melanoma tumor has metastasized, it is classified as a stage III or IV melanoma depending in on the degree of metastasis.

NLRP3 (NOD-like receptor family, pyrin domain containing 3), also known as NALP3 or cryopyrin, is one of the sensors of the inflammasome, a macromolecular structure involved in interleukin-1β (IL-1β) and IL-18 processing. NLRP3 senses intracellular danger during intracellular infections (bacterial and viral proteins) or tissue injury (ischemia). NLRP3 activation leads to recruitment of ASC (apoptosis-associated speck-like protein containing carboxyterminal caspase recruitment domain) and caspase-1 leading to inflammasome formation and ultimately cell death.

There is a need for a method for treating melanoma. The method should be effective and have no significant side effects.

DETAILED DESCRIPTION OF THE INVENTION

Activation of the NLRP3 inflammasome amplifies the inflammatory response to tissue injury and mediates further damage. Dapansutrile is a selective NLRP3 inflammasome inhibitor; dapansutrile reduces inflammation by preventing activation of the NLRP3 inflammasome. Dapansutrile inhibits the production of mature IL-1β and IL-18 in mice and in human cells in vitro. Through this mechanism of action, dapansutrile prevents production and/or release of IL-1β and inhibits the formation of NLRP3 inflammasome in animals and human subjects.

The inventors have discovered that by preventing the production of IL-1β, dapansutrile provides the following effects: reduces angiogenesis, reduces IL-1 dependent vascular endothelial growth factor (VEGF) production, limits generation of myeloid-derived suppressor cells (MDSCs), prevents elevation of IL-8 levels, inhibits migration of endothelial precursors into tumors, reduces levels of IL-6, and other stromal factors, reduces accumulation of neutrophils in tumor sites, reduces production of growth factors such as granulocyte-macrophage colony stimulating factor (GM-CSF), FGF, and IL-1, reduces expression of matrix metalloproteinase (MMP) and cyclooxygenase production. By reducing IL-1β production, dapansutrile reduces effects induced by IL-1.

MDSCs are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Expansion of myeloid derived cells (MDSCs) is generally linked to chronic inflammation (10, 11), and MDSCs have been shown to play a major role in cancer-mediated immunosuppression (12). In melanoma patients, high levels of MDSCs (both PMN- and M-MDSCs) correlate with stage, metastasis and poor outcomes compared to subjects with lower number of these cells (13).

The inventors have demonstrated that dapansutrile reduces melanoma tumor volume in mice and maintains the MDSC levels in mice having melanoma compared to those observed in wild-type with no tumor. This occurs because dapansutrile prevents MDSC expansion and restores the physiological levels of these cells.

The inventors have demonstrated that melanoma tumor-bearing mice fed with dapansutrile-enriched diet show decreased circulating levels of IL-6, G-CSF, and VEGF compared to the tumor-bearing mice fed with standard diet.

The mechanisms of metastasis involve a complex multi-step process of detachment from the primary tumor site, intravasation into circulation, survival in the circulation, extravasation from circulation, attachment at a secondary site, and development of secondary tumor sites, each of which involve mediators induced by IL-1β (23, 24). The inventors have demonstrated that tumor-bearing mice treated with dapansutrile show reduced metastasis in both the lung and liver.

Angiogenesis, a hallmark of tumor growth, is associated with an abundance of infiltrating immune cells and the induction of pro-angiogenic factors like VEGF, thus linking chronic inflammation with angiogenesis. The inventors have demonstrated that dapansutrile reduces the inflammatory events that are linked to angiogenesis, reduces circulating VEGF plasma levels, and reduces tumor angiogenesis.

Immunotherapy has provided dramatic advances in the treatment of advance stage of melanoma and is becoming the standard of care. Combination immunotherapy with anti-PD-1 (nivolumab) and CTLA-4 (ipilimumab) results in tumor regressions with more than 50% response rate (7). Nevertheless, immunotherapy is often associated with toxicity such as immunotherapy-related adverse events (irAEs) (8) and the number of non-responders and relapsed cases continues to be an important and unmet clinical need in melanoma treatment. The inventors have demonstrated that combinational therapy with an anti-PD-1 antibody and dapansutrile provides enhanced efficacy versus the anti-PD-1 monotherapy in reducing tumor growth.

The inventors believe that dapansutrile is effective to prevent melanoma growth by blocking the assembly of the NLRP3 inflammasome and preventing the production and/or release of IL-1β. By preventing IL-1β processing in melanoma cells, dapansutrile provides a new therapy for melanoma and immunotherapy-resistant cancers. Dapansutrile reduces many hallmarks of cancer: tumor growth, immune suppression, inflammation, metastasis, and angiogenesis, and thus it provides a new cancer therapy.

The present invention is directed to methods of treating melanoma, such as superficial spreading melanoma, nodular melanoma, lentigo maligna melanoma, and acral lentiginous melanoma.

Compound

The present invention uses a purified compound of dapansutrile (3-methanesulfonyl-propionitrile), or the pharmaceutically acceptable salts or solvate thereof:

Dapansutrile is a small, synthetic molecule of β-sulfonyl nitrile which has been demonstrated to selectively inhibit the NLRP3 inflammasome and be safe when orally administered to healthy subjects (9).

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$(wherein X is $C_{1-4}$).

"Solvates," as used herein, are addition complexes in which the compound is combined with an acceptable co-solvent in some fixed proportion. Co-solvents include, but are not limited to, water, acetic acid, ethanol, and other appropriate organic solvents.

Pharmaceutical Compositions

The active compound dapansutrile, or its pharmaceutically acceptable salt or solvate in the pharmaceutical compositions in general is in an amount of about 0.1-5% for an injectable formulation, about 1-90% for a tablet formulation, 1-100% for a capsule formulation, about 0.01-20%, 0.05-20%, 0.1-20%, 0.2-15%, 0.5-10%, or 1-5% (w/w) for a topical formulation, and about 0.1-5% for a patch formulation.

"About" as used in this application, refers to ±10% of the recited value.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of dapansutrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but are not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of dapansutrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including dapansutrile can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent). In one embodiment, diethylene glycol monoethylether is included in the topical gel formulation.

Method of Use

By inhibiting assembly of the NLRP3 inflammasome, dapansutrile prevents the production and/or release of proinflammatory cytokines IL-1β and IL-22, and ultimately reduces melanoma growth in mice.

In addition, dapansutrile inhibits the processing and release of IL-1β and IL-18, but not the synthesis of the IL-1β precursor and the other inflammasome components including NLRP3 and ASC. Dapansutrile also inhibits caspase-1 activation. Moreover, dapansutrile preserves the body's immune surveillance by not suppressing other inflammasomes such as NLRC4 and AIM2, constitutive cytokines and by protecting from cell death.

The present invention is directed to methods of preventing and/or treating melanoma, such as superficial spreading melanoma, nodular melanoma, lentigo maligna melanoma, and acral lentiginous melanoma. The above types of melanoma have an inflammatory component either as a cause of the disease or as a result of an event. The method comprises the step of administering to a subject in need thereof an effective amount of dapansutrile. "An effective amount," as used herein, is the amount effective to treat a disease by ameliorating the pathological condition, and/or reducing, improving, and/or eliminating the symptoms of the disease. For example, an effective amount is an amount that reduces the growth of melanoma (reducing tumor size).

Immunotherapy has significantly improved the standard of care for melanoma patients; however, non-responders and the number of relapsing patients are still very high. Therefore, combination therapies that increase the efficacy of checkpoint inhibitors represent an important clinical benefit. In one embodiment, the present invention is directed to a combination therapy by combining dapansutrile and a checkpoint inhibitor such as anti-PD-1 antibody for treating melanoma. The method comprising administering an effective amount of dapansutrile and an effective amount of anti-PD-1 antibody to a subject in need thereof. Dapansutrile and anti-PD-1 antibody can be administered simultaneously or sequentially. It is advantageous to co-administer dapansutrile with anti-PD-1 antibody because dapansutrile improves the efficacy of anti-PD-1 and dapansutrile has a safe drug profile. The co-administration may also reduce the required dosage of anti-PD-1 antibody, which reduces immunotherapy-related adverse events.

The combination treatments with dapansutrile and anti-PD-1 inhibit tumor-induced immunosuppression and increase T-cell activity simultaneously. Furthermore, increase in inflammatory cytokines such as IL-6 has been associated with the pathophysiology of irAEs. Danpansutrile enhances the effect of the anti-PD-1 and further reduces the circulating levels of IL-6, a marker for poor prognosis in melanoma. Combination therapy also enhances tumor-specific Th1 responses, which suggests less tumor-induced immunosuppression and more T cell activation leading to a stronger anti-tumor response. Thus, the treatment with dapansutrile in addition to anti-PD-1 potentiates the effect of a single therapy, creating an alternative for therapy-resistant cancers.

The pharmaceutical composition of the present invention can be applied by systemic administration or local administration. Systemic administration includes, but is not limited to oral, parenteral (such as intravenous, intramuscular, subcutaneous or rectal), and inhaled administration. In systemic administration, the active compound first reaches plasma and then distributes into target tissues. Oral administration is a preferred route of administration for the present invention. Local administration includes topical administration.

Dosing of the composition can vary based on the extent of the subject's melanoma and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

In one embodiment, the pharmaceutical composition is administrated orally to a subject. The dosage for oral administration is generally 0.1-100, 0.1-20, or 1-100 mg/kg/day, depending on the subject's age and condition. For example, the dosage for oral administration is 0.1-10, 0.5-10, 1-10, 1-5, 5-50, or 5-100 mg/kg/day for a human subject. In one embodiment, the active compound can be applied orally to a human subject at 10-100, 10-500, 20-2000, 50-2000, or 100-2500 mg/dosage, 1-4 times a day, depends on the patient's age and condition.

In one embodiment, the pharmaceutical composition is administrated intravenously to a subject. The dosage for intravenous bolus injection or intravenous infusion is generally 0.03 to 5 or 0.03 to 1 mg/kg/day.

In one embodiment, the pharmaceutical composition is administrated subcutaneously to the subject. The dosage for subcutaneous administration is generally 0.3-20, 0.3-3, or 0.1-1 mg/kg/day.

In one embodiment, the composition is applied topically. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically, 0.2-10 mL of the topical composition is applied to the individual per dose.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

The following protocols were used in the experiments described below.

Abbreviations. IL-1β (Interleukin 1 beta), IL-6 (Interleukin 6), G-CSF (Granulocyte colony-stimulating factor), VEGF (Vascular endothelial growth factor), IL-22 (Interleukin 22), IL-17 (Interleukin 17), PMN-MDSC (polymorphonuclear MDSC), M-MDSC (Monocytic MDSC), PD-1 (programmed cell death protein 1), MCM (melanoma conditioned media), HUVEC (human umbilical vein endothelial cells), PBMCs (peripheral blood mononuclear cells), VWF (Von Willebrand Factor).

Cell culture. 1205Lu human melanoma cells were cultured in RPMI. Each was supplemented with 10% FBS, 100 units/mL penicillin, 0.1 mg/ml streptomycin. Cells were maintained in a humidified 5% $CO_2$ atmosphere at 37 C. Human metastatic melanoma cell line 1205Lu were plated in RPMI at $2.5\times10^5$ per well in a 24-wells plate and allowed to adhere overnight. The following day, media was replaced with fresh RPMI 10% FBS with or without OLT1177® (dapansutrile). For the induction of cytokine production IL-1α (20 ng/ml) was used. OLT1177® was added 30 minutes prior to stimulation. Supernatants were collected, in both unstimulated and stimulated conditions at 24 hours.

1205Lu NLRP3 siRNA. 1205Lu cells ($2\times10^5$) were incubated with siRNA targeting NLRP3 or scrambled siRNA for non-specific gene silencing (Santa Cruz Biotechnology). Transfection of the siRNA duplexes (2 nM) was carried out using siRNA Transfection Medium according to the manufacturer's instructions. After 24 hours, the medium was replaced with RPMI 10% FBS (500 μl), and the cells were incubated for additional 24 hours. The supernatants were collected for the measurement of IL-1β levels by ELISA. Efficacy of the NLRP3 silencing was determined by Western blotting in the cell lysates.

Cytokine measurements. Cytokines in supernatants and cell lysates were measured by specific ELISA according to the manufacturer's instructions (DuoSet, R&D Systems, Minneapolis, MN).

Melanoma conditioned media assays. PBMCs were isolated from consenting healthy donors in accordance to COMIRB and plated at ($5\times10^5$) per well in a 96-well plate. Supernatants from 1205Lu cells treated with OLT1177® were then added to PBMCs (1:2) and cells were incubated for 72 hours. NLRP3 deficient THP-1 cells ($1\times10^5$) were plated out in a 96-well plate and activated with 10 ug/mL of LPS for 3 hours. MCM was then added (1:2) to wells as stimulation. Cells were incubated for 3 days and supernatants were assayed for cytokine secretion.

Angiogenesis assay (HUVEC). HUVEC cells were seeded on media with no growth factors overnight. Cells were plated onto Matrigel (Corning) coated wells at $8\times10^4$ cells per well in a 24 well plate. Cells were then incubated for 5 hours in the presence of HUVEC complete media (control), MCM or MCM in which 1205Lu cells were treated with OLT1177®. MCM was added without dilution. Media was then removed and matrigel was preserved in PFA4%. Pictures were taking at 40× and branching points were counted using the cross method.

Combo Therapy Model. B16F10 cells were injected as described. Four days after instillation of Matrigel plug, mice were started on OLT1177® diet or continued on standard diet and at day 7 a neutralizing antibody against PD-1 (200 ug/mouse; BioXCell, West Lebanon, NH) was injected peritoneally. Mice were sacrificed following 15 days from the B16F10 instillation.

Tumor Angiogenesis Model. A mixture of Matrigel and B16F10 ($2\times10^5$) was inoculated s.c. in the interscapular area of mice fed standard or OLT1177® diet. Following 7 days from the implantation, the plugs were removed, fixed in 4% paraformaldehyde, embedded in paraffin and sectioned (4 μm). Following, the sections were de-paraffinized, hydrated and stained with hematoxylin/eosin. Separate sections were subjected to heat-induced antigen retrieval (10 mM Citrate 0.05% Tween 20-pH 6.0) at 95° C. for 15 min. The sections were then placed in a humidified slide chamber, blocked for 1 h in 10% normal donkey serum (Jackson Immunologicals) and immunostained using an antibody for Von Willebrand factor (1:100, Millipore-Sigma, Burlington, MA) overnight at 4° C. for identification of new vessel formation. Anti-rabbit horseradish peroxidase enzyme (HRP) conjugated antibody (1:100, Jackson ImmunoResearch Laboratories, West Grove, PA) were used as secondary antibody for 2 hours at room temperature. Sections were then incubated for 5-10 min with HRP substrate as directed by the manufacturer's instructions (NovaRED substrate, Vector Laboratories, Burlingame, CA). Nuclei counterstaining were achieved using Mayer's Hematoxylin counterstaining (Thermo Fisher scientific Waltham, MA).

Metastasis Model. Metastasis formation was determined following tail intravenous (i.v.) injection of B16F10-GFP ($1 \times 10^6$) cells in mice fed standard or OLT1177® diet. Before injection, the B16F10-GFP+ cells were sorted by flow cytometry and only the top brightest 10% cells were injected. Mice were sacrificed after 21 days from the cell injection and lung and liver were isolated and prepared for histology. Previous isolation, lungs were inflated with a solution containing 0.5% low melting agarose to avoid the tissue from collapsing. The presence of GFP-positive cell in the lung and liver of tumor bearing mice were performed by fluorescent microscopy. Tissue sections were stained with Alexa Fluor conjugated WGA, for membranes detection and DAPI, for nuclear stain. Images were acquired blindly and randomly across the tissue sections to obtain 7-10 images per tissue section. GFP positive cells were counted in each image and the results reported as number of GFP+ cells/field area (full chip field).

Statistical Analysis. Statistical significance of differences was evaluated with a two-tailed Student's t test using Prism version 7.0 software (GraphPad Software, La Jolla, CA, USA). Statistical significance was set at $p<0.05$.

Example 1. Dapansutrile Reduces Tumor Growth and Tumor-Induced Inflammation

C57BL/6J male mice, 6-8 weeks old (The Jackson Laboratory), were fed ad libitum with either a standard diet or a diet containing OLT1177® (dapansutrile) at a dose of 7.5 g per Kg of food for one week before subcutaneous instillation of a mixture of Matrigel and B16F10 cells ($2 \times 10^5$) on the hind quarter of the mice. The dosage was approximately 100 mg/kg/day based on feed concentrations of 7.5 g/kg and food consumption of 4 g/day. These diets were continued after tumor implantation. Mice were sacrificed following 15 days from the plug instillation. Tissue and plasma were assessed after 15-day post-inoculation.

Figure 1A:
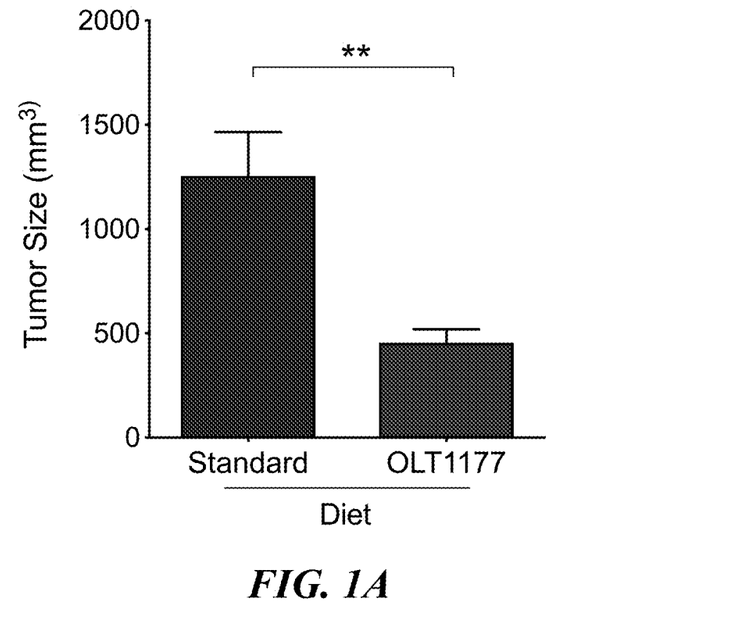
FIGS. 1A-1E show OLT1177® (dapansutrile) reduces tumor volume and melanoma-associated inflammation. (1A) Tumor size in mice fed with standard or OLT1177® diet (N=15). (1B) Mean±SEM of plasma IL-6 in tumor-bearing mice fed with standard or OLT1177® diet (N=6 per group). (1C) Mean±SEM of plasma G-CSF in mice fed with standard or OLT1177® diet (N=4-5 per group). (1D) Intracellular cytokine staining for IL-22 from spleen-derived cells of mice fed with standard or OLT1177® diet. (1E) Intracellular cytokine staining for IL-17 from spleen-derived cells of mice fed with standard or OLT1177® diet. **$p<0.01$, *$p<0.05$.

Tumor-bearing mice fed OLT1177® diet displayed reduced tumor volume when compared to mice fed standard diet (FIG. 1A).

Figure 1B:
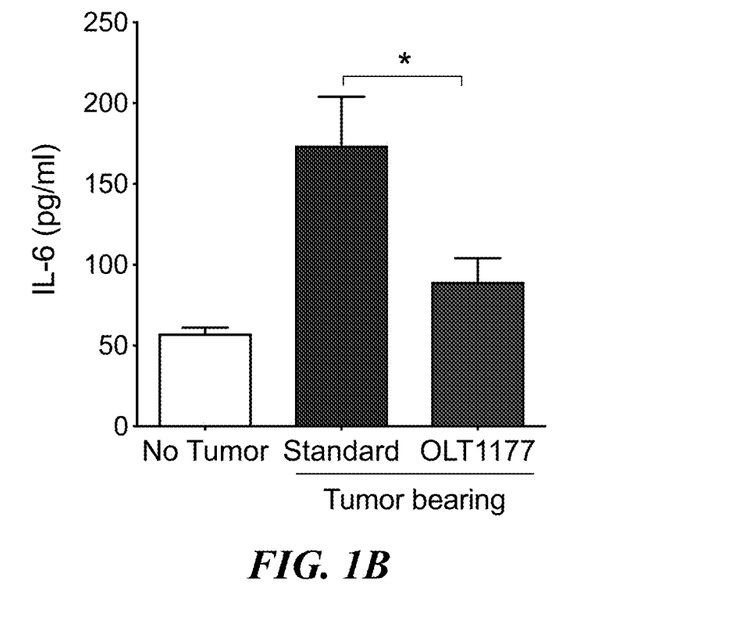
Figure 1C:
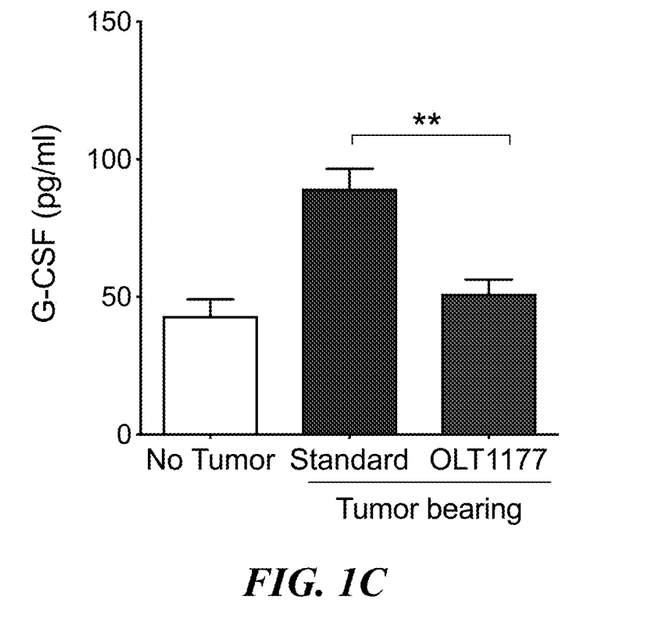

Tumor-bearing mice fed standard diet, exhibited significantly higher plasma levels of IL-6 (FIG. 1B) and significantly higher plasma levels of granulocyte-colony stimulating factor (G-CSF, FIG. 1C) compared to non-tumor bearing mice. In mice fed the OLT1177® diet, these levels were significantly reduced (FIG. 1B, 1C).

In vivo, increased levels of circulating IL-6 and G-CSF were observed in tumor-bearing mice when compared to the non-tumor-bearing group, confirming the association of melanoma progression with inflammation. Treatment with dapansutrile significantly limited these inflammatory mediators. Consistent with reduction in systemic inflammation, treatment with OLT1177 showed a reduction in tumor volume.

Figure 1D:
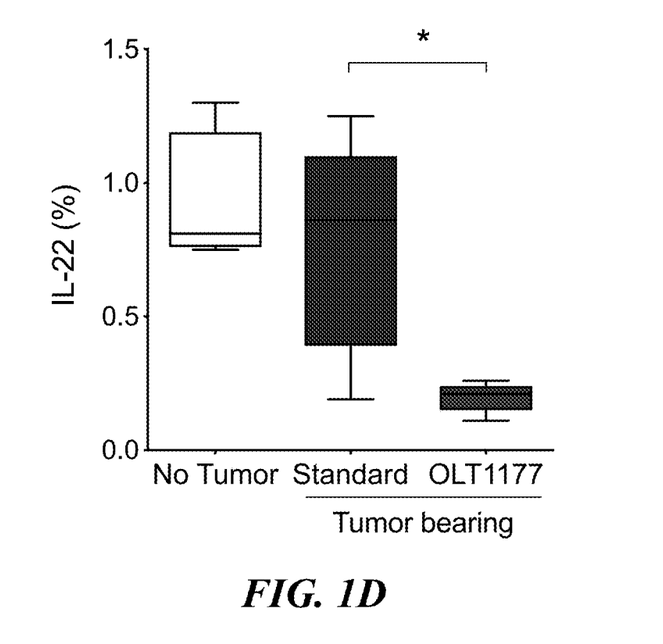
Figure 1E:
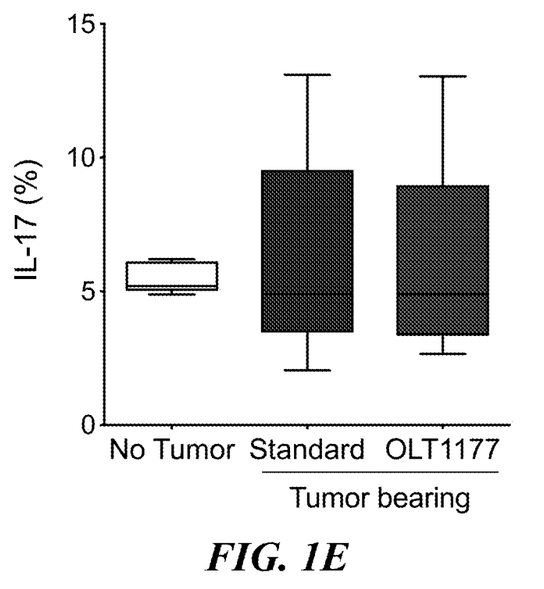

Intracellular cytokine staining (ICCS) in spleen-derived T cells showed reduced IL-22 levels in tumor bearing mice on OLT1177® diet compared to the mice fed standard diet (FIG. 1D). No changes were observed for IL-17 (FIG. 1E).

These data show that oral treatment by dapansutrile results in a reduction in tumor volume and melanoma-associated inflammation.

Example 2. Dapansutrile Reduces Endothelial Function and Angiogenesis

Figure 2A:
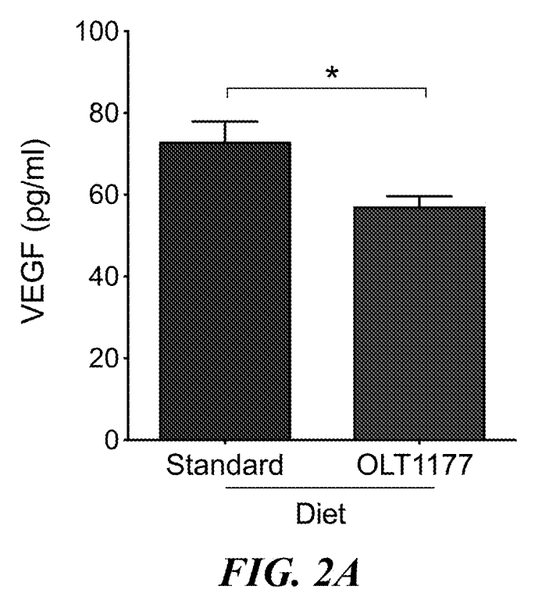
FIGS. 2A-2C show that dapansutrile reduces endothelial function and angiogenesis. (2A) Mean±SEM of plasma VEGF in tumor bearing mice fed with standard or OLT1177 diet (N=4-5 per group). (2B) Representative images of endothelial cell activation in matrigel plugs stained for Von Willebrand Factor (depicted by arrows) which reflects formation of new vessels from mice fed with standard or OLT1177® diet (each picture represents a single mouse). (2C) Mean±SEM of tubular like structures by HUVECs following stimulation with melanoma conditioned media (MCM) in presence and absence of OLT1177®. *$p<0.05$.

We next determined the ability of dapansutrile on inhibition of angiogenesis, an acquired ability of tumor cells to sustain a blood supply to nourish the growing tumor mass. Matrigel plugs containing B16F10 melanoma cells were injected into mice on diets as described above. After seven days to allow endothelial cell infiltration, plugs were removed, and plasma VEGF levels were determined. As shown in FIG. 2A, mice receiving the OLT1177® diet showed significantly lower circulating VEGF levels compared to the tumor-bearing mice fed standard diet.

Figure 2B:
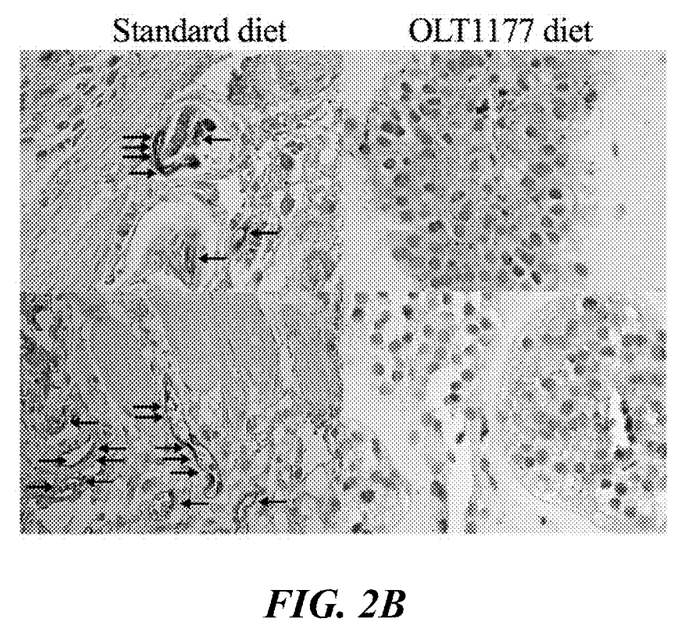

To further investigate the effect of dapansutrile's inhibition on angiogenesis in vivo, the matrigel plugs were collected and immunohistochemistry for Von Willebrand Factor (VWF) was performed to determine new blood vessels formation. As illustrated in FIG. 2B, plugs derived from the OLT1177® fed mice revealed reduced VWF stained endothelial cells compared to the mice fed the standard diet.

Figure 2C:
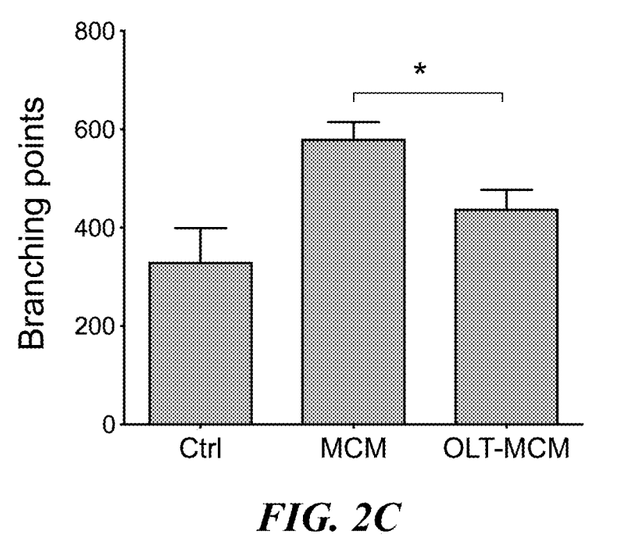

The effects of dapansutrile on angiogenesis was determined in vitro using human umbilical vein endothelial cells (HUVEC). MCM promoted formation of tubular-like structure in HUVEC seeded on Matrigel, mimicking in vivo neoangiogenesis when compared to the control condition. MCM derived from 1205Lu cells treated with OLT1177® significantly reduced HUVEC orientation as shown by the reduced number of branching points FIG. 2C). These studies are consistent with the role of IL-1β in promotion of angiogenesis and the expression of VEGF and VEGF Receptors in mouse melanoma models, including endothelial cell branching.

Angiogenesis, a hallmark of tumor growth, is associated with an abundance of infiltrating immune cells and the induction of pro-angiogenic factors like VEGF, thus linking chronic inflammation with angiogenesis. Here we show that stimulation of HUVECs seeded on matrigel with MCM derived from 1205Lu cells treated with dapansutrile resulted in reduced number of tubular like structures compared the cells in control. Furthermore, mice fed with dapansutrile diet showed a reduction in circulating VEGF when compared to mice fed with standard diet. Histological analysis showed that the implanted matrigel plugs imbedded with B16F10 cells contained a reduced number of new vessels as measured by Von Willebrand Factor stain. These data suggest that systemic treatment by dapansutrile reduces the inflammatory events that are linked to angiogenesis, and it provides a reduction in angiogenesis.

Example 3. Dapansutrile Reduces Tissue Invasion and Metastasis

The mechanisms of metastasis involve a complex multi-step process of detachment from the primary tumor site, intravasation into circulation, survival in the circulation, extravasation from circulation, attachment at a secondary site, and development of secondary tumor sites.

To determine whether dapansutrile reduces tissue invasion and metastasis, B16F10-GFP labeled cells were injected intravenously in mice fed with standard or OLT1177® diets.

Figure 3A:
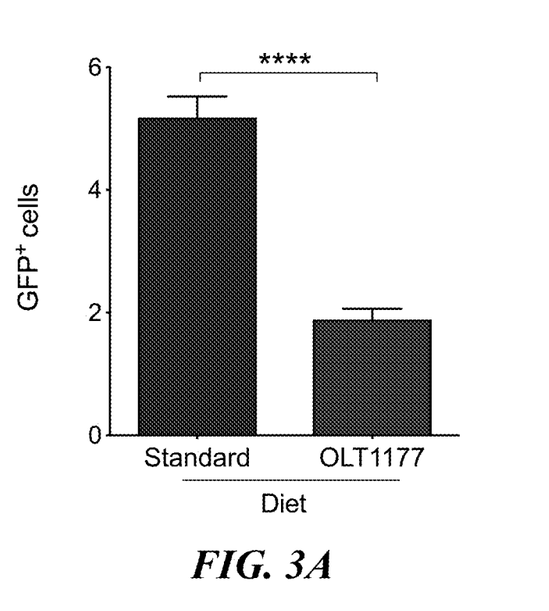
FIGS. 3A-3B show that dapansutrile reduces tissue invasion and metastasis in lung and liver (3A). Mean±SEM of B16F10-GFP$^+$ cell counts/field area (full chip field) in the lungs from tumor-bearing mice receiving standard or OLT1177® diet, assessed by blinded microscopist (N=3 per group). **$p<0.0001$, $p<0.01$, *$p<0.05$. (3B) Mean±SEM of blinded GFP+ cell counts in the livers from tumor-bearing mice receiving standard or OLT1177® diet (N=3 per group). ****$p<0.0001$.
Figure 3B:
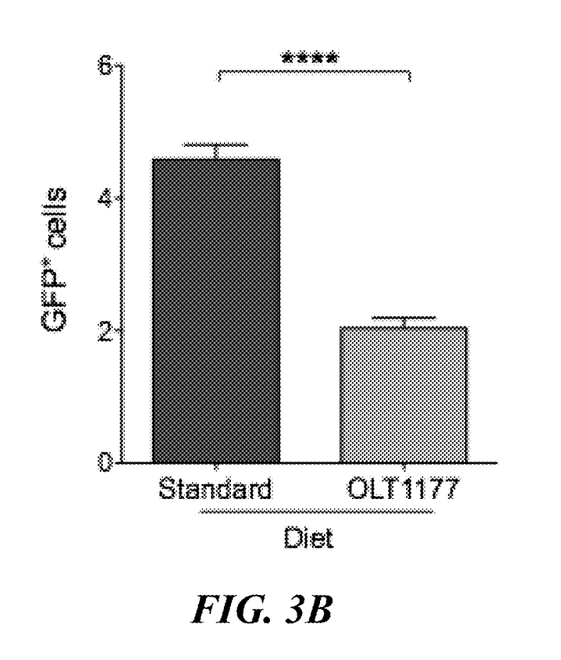

Immunofluorescence analysis of the lungs and the livers showed reduced number of GFP$^+$ cells in mice that received OLT1177® compared to the standard diet. In FIG. 3A, the number of GFP$^+$ cells in the lungs is reduced by 66% (p<0.0001) by dapansutrile treatment. A similar reduction (−60%; p<0.001) in the number of GFP$^+$ B1610 cells was observed in the liver (FIG. 3B). Together, the reductions in the number of metastatic cells in the lung and liver indicate that dapansutrile reduces tissue invasion and reduces the metastasis in both liver and in lung.

Example 4. Dapansutrile Reduces Tumor Progression by Limiting Expansion of MDSCs Tumor progression and immune system evasion often correlate with the tumor-induced expansion of MDSCs (27, 28). Two populations have been characterized: PMN-MDSCs and M-MDSCs (29).

Figure 4A:
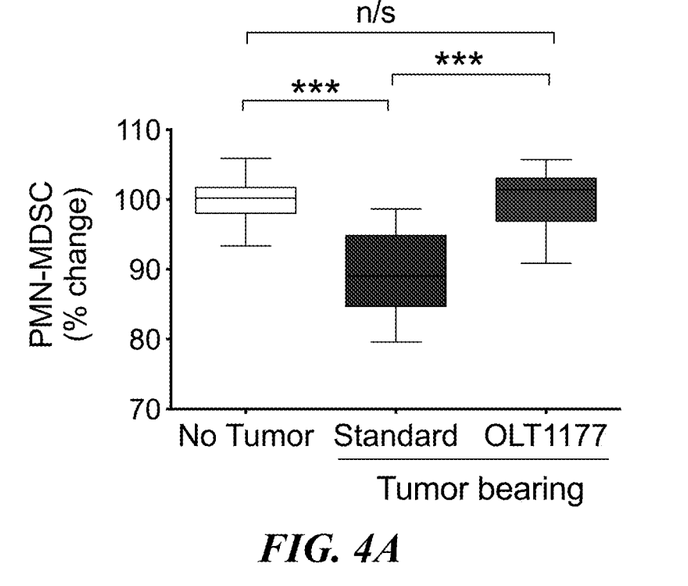
FIGS. 4A-4F show that dapansutrile reduces expansion of MDSCs. (4A) Bone marrow, (4B) spleen, and (4C) lymph node level of PMN-MDSC (CD11b$^+$Ly6G$^+$Ly6C$^{lo}$) in non-tumor-bearing mice (No tumor) compared to tumor-bearing mice fed either standard (Standard) or OLT1177® diet. (4D) Bone marrow, (4E) spleen, and (4F) lymph node level of M-MDSC (CD11b$^+$Ly6G$^-$Ly6C$^{hi}$) in non-tumor-bearing mice (No tumor) compared to tumor-bearing mice receiving either standard (Standard) or OLT1177® diet. Data are expressed as percent change of MDSCs in non-tumor-bearing mice (No tumor) set at 100. (N=8-10 per group). ***$p<0.001$, *$p<0.05$.
Figure 4B:
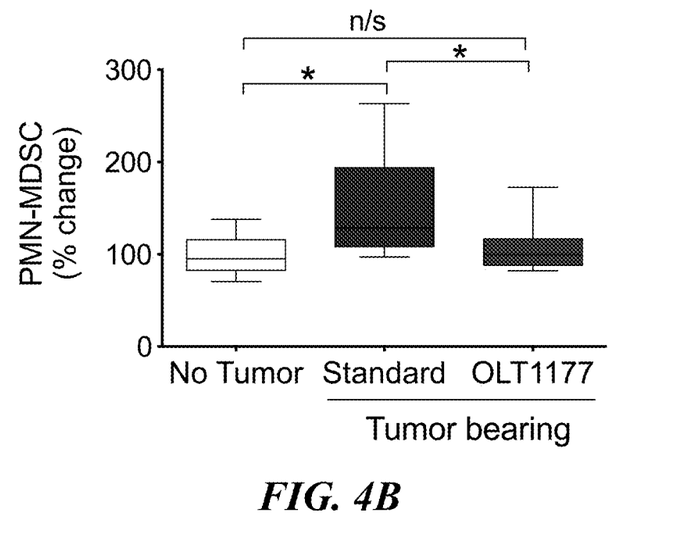
Figure 4C:
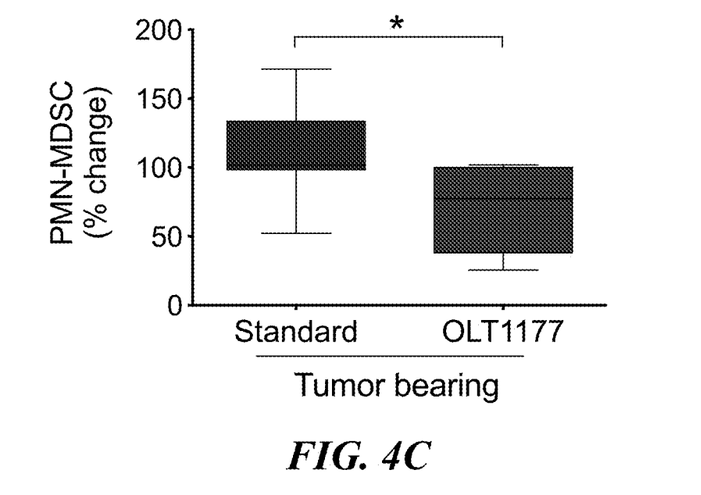
Figure 4D:
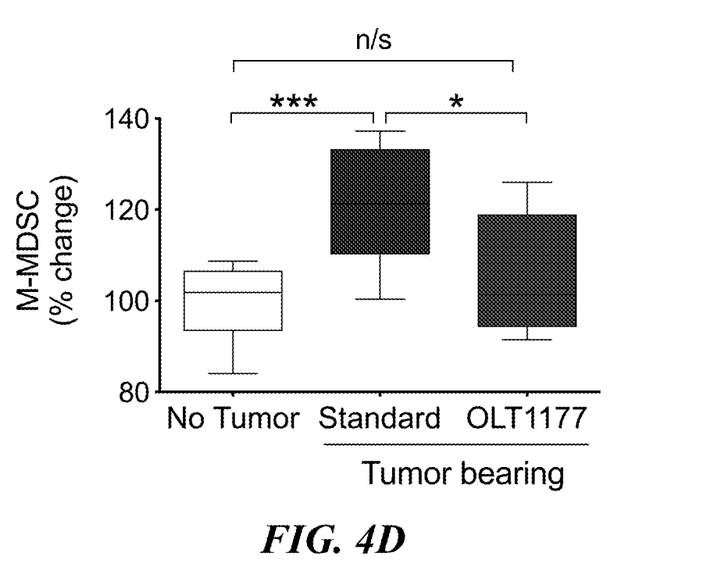
Figure 4E:
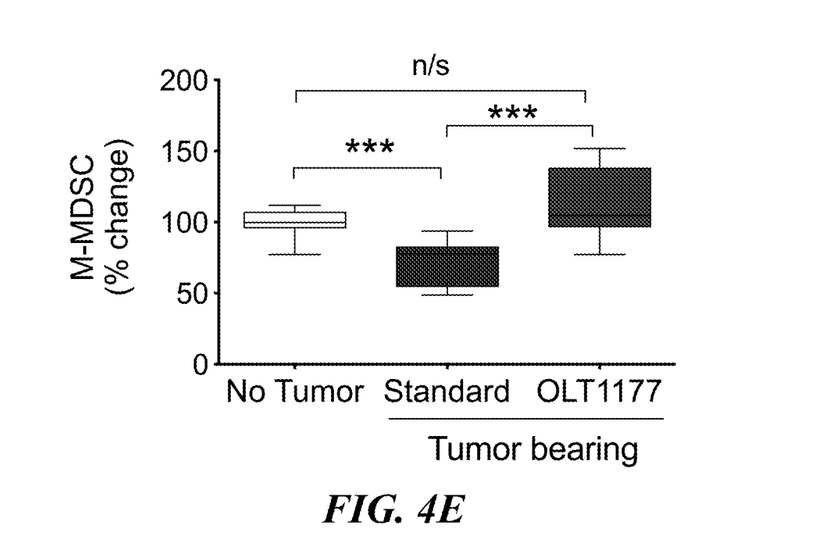
Figure 4F:
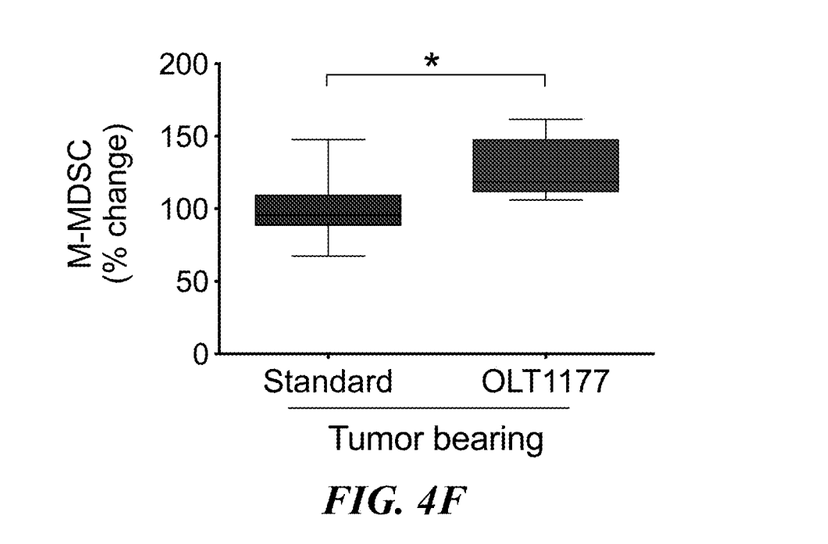

Flow cytometry analysis was used to assess the effect of NLRP3 inhibition on the activation and expansion of MDSCs, key mediators of tumor-associated immunosuppression. Bone marrow, spleen, and lymph node-derived cells were isolated and analyzed for the two main MDSCs subtypes: polymorphonuclear MDSCs (PMN-MDSC) expressing CD11b$^+$Ly6G$^+$Ly6C$^{lo}$ and monocytic MDSCs (M-MDSC) expressing CD11b$^+$Ly6G$^-$Ly6C$^{hi}$. Bone marrow cells from tumor-bearing mice showed reduced PMN-MDSCs compared to non-tumor-bearing mice (FIG. 4A). In the spleen, the level of PMN-MDSCs in tumor-bearing mice was increased compared to non-tumor-bearing mice (FIG. 4B). However, in mice fed the dapansutrile diet, we observed a restoration of the PMN-MDSC population at the level observed in the non-tumor-bearing mice (FIGS. 4A-4B). Analysis of the lymph nodes revealed reduction in PMN-MDSCs in mice fed with the dapansutrile diet compared to the standard diet (FIG. 4C). Analysis of the M-MDSCs population in the bone marrow, spleen and lymph nodes showed an inverted profile compared to the PMN-MDSCs in tumor-bearing mice versus non-tumor-bearing mice. As depicted in FIGS. 4D-4F, tumor-bearing mice fed standard diet exhibited increased M-MDSCs cells in the bone marrow and reduced levels in the spleen and lymph nodes when compared to the non-tumor-bearing mice. Treatment with dapansutrile prevented the tumor-induced effect on M-MDSCs expansion, normalizing the population to the non-tumor-bearing mice level (FIGS. 4D-4F).

Here we observe that inhibition of the NLRP3 inflammasome in mice fed with dapansutrile diet reversed the populations of MDSCs back to the populations present in non-tumor bearing mice lacking chronic or tumor-associated inflammation. These findings suggest dapansutrile is effective in reversing tumor-induced immunosuppression in melanoma. Moreover, we observed different tumor-induced changes in PMN-MDSCs and M-MDSCs expansion compared to the non-tumor-bearing mice. It appears that PMN-MDSCs migrates from the bone marrow to infiltrate peripheral tissue like spleen and lymph nodes while M-MDSCs have increased expansion in the bone marrow. Here we show that spleen-derived T-cells stimulation from tumor bearing mice treated with dapansutrile expressed significant lower IL-22 levels. These results are consistent with the reduction on tumor growth observed in the tumor bearing mice treated with dapansutrile.

Figure 5A:
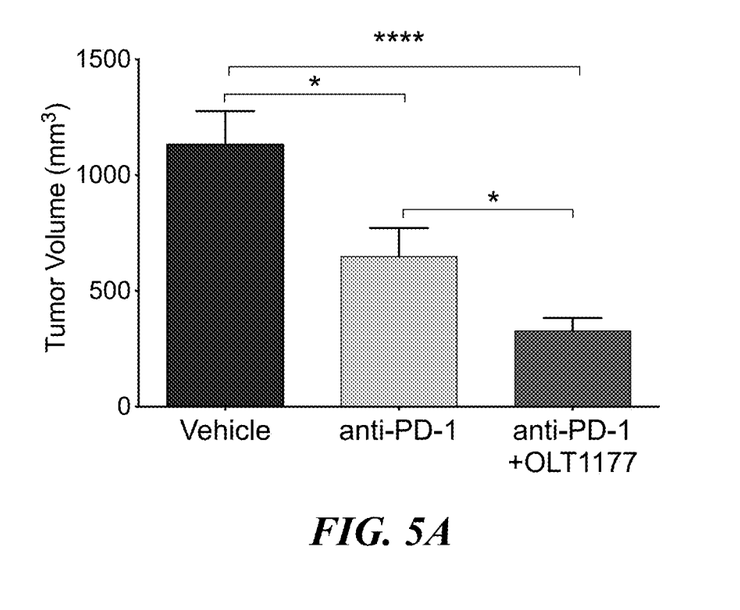
FIGS. 5A-5D show that dapansutrile enhances the efficacy of anti-PD-1 blockade. (5A) Tumor size in tumor-bearing mice for vehicle, anti-PD-1 and anti-PD-1+ OLT1177® diet treated mice (N=13). (5B) Mean±SEM of plasma IL-6 in tumor-bearing mice shown in A (N=8-9). (5C) Mean±SEM of whole blood lysates for MPO in tumor-bearing mice shown in A (N=11). (5D) NK T cell (CD3$^+$CD8$^-$CD161$^+$CD335$^+$) infiltration in primary tumors in mice shown in A (N=5). **p<0.0001, *p<0.001, **p<0.01, *p<0.05.

Example 5. Anti-PD-1 and OLT1177 Combination Therapy Results in Increased Anti-Tumor Efficacy We evaluated the effect of dapansutrile in combination with the standard of care for immunotherapy, using an antibody against PD-1. Mice were placed on standard diet and injected subcutaneously with B16F10 cells (experimental day 0). Four days after the B16F10 instillation, mice were started on the OLT1177® diet or were kept on standard diet. Three days later (experimental day 7), mice were injected intraperitoneally with an anti-PD-1 antibody. As shown in FIG. 5A, treatment with OLT1177® before anti-PD-1 significantly reduced tumor size compared to anti-PD-1 alone. The reduction in tumor volume with anti-PD-1 was 43% (p<0.05) whereas the combined therapy reduced the tumor size by 72% compared to vehicle (p<0.0001).

Figure 5B:
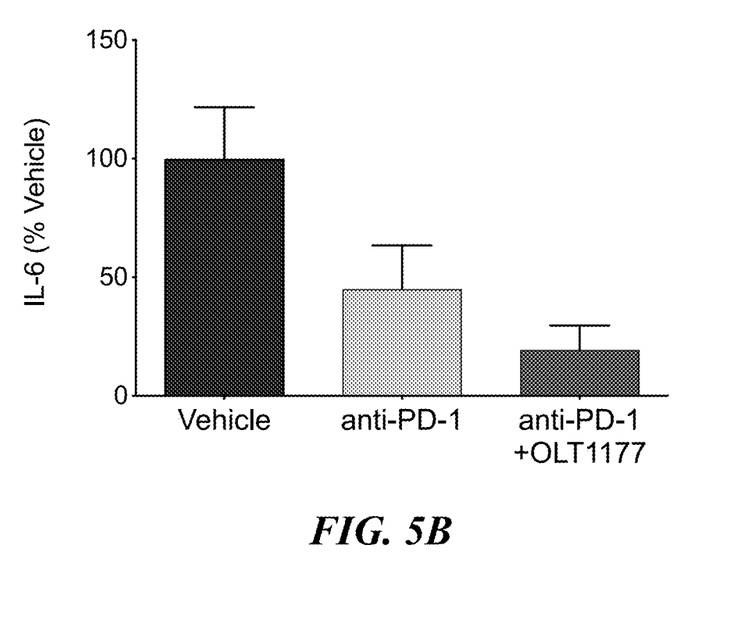
Figure 5C:
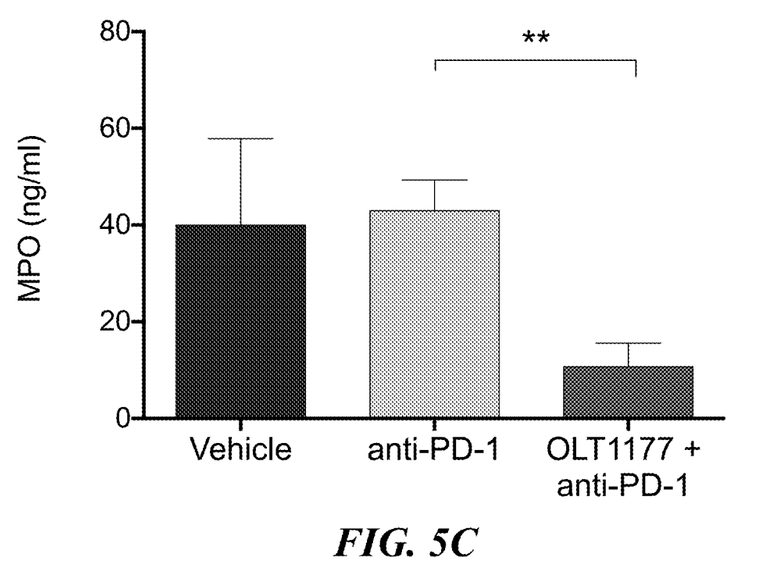
Figure 5D:
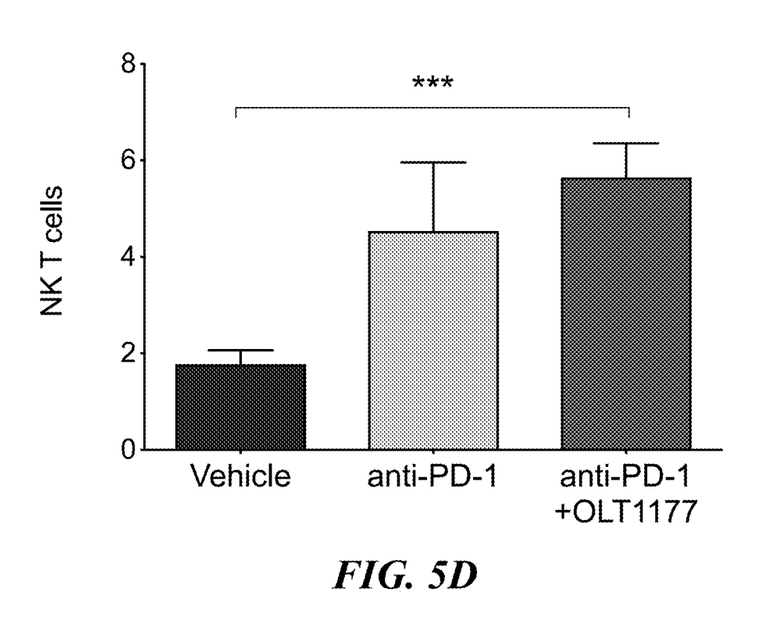

Also, we observed a trend in reduction of circulating IL-6 in the combination therapy compared to single treatment (−25.3%, p=0.2, FIG. 5B). Whole blood lysates revealed a drastic decrease in myeloperoxidase (MPO) in the tumor-bearing mice receiving the combination therapy compared to the monotherapy (FIG. 5C). OLT1177® and anti-PD-1 treatment also showed a trend toward increased NK cells in the primary tumor when compared to the anti-PD-1 treatment alone (FIG. 5D). These data suggest that the combination of dapansutrile treatment with a checkpoint inhibitor increases the anti-tumor immune response compared to the immunotherapy alone.

It is to be understood that the foregoing describes preferred embodiments of the present invention and that modifications may be made therein without departing from the scope of the present invention as set forth in the claims.

REFERENCES

1. Y. Guo, et al. Cancer Res 77, 6429-6441 (2017).
2. S. Shalapour, et al. J Clin Invest 125, 3347-3355 (2015).
3. C. A. Dinarello. Blood 117, 3720-3732 (2011).
4. R. N. Apte, et al. Cancer Metastasis Rev 25, 387-408 (2006).
5. C. A. Dinarello. Cancer Metastasis Rev 29, 317-329 (2010).
6. B. Guo, et al. Sci Rep 6, 36107 (2016).
7. D. N. Khalil, et al. Nat Rev Clin Oncol 13, 273-290 (2016).
8. M. A. Postow, et al. N Engl J Med 378, 158-168 (2018).
9. C. Marchetti, et al. Proc Natl Acad Sci USA 115, E1530-E1539 (2018).
10. C. R. Millrud, et al. Oncotarget 8, 3649-3665 (2017).
11. S. Ostrand-Rosenberg, et al. J Immunol 182, 4499-4506 (2009).
12. V. Umansky, et al. Vaccines (Basel) 4, E36 (2016).
13. K. R. Jordan et al., Cancer Immunol Immunother 62, 1711-1722 (2013).

What is claimed is:

1. A method of treating melanoma in a subject, comprising the step of:
   administering to the subject suffering from the melanoma an effective amount of dapansutrile, or a pharmaceutically acceptable solvate thereof.

2. The method according to claim 1, wherein the melanoma is selected from the group consisting of: superficial spreading melanoma, nodular melanoma, lentigo maligna melanoma, and acral lentiginous melanoma.

3. The method according to claim 1, wherein dapansutrile is administered by systemic administration.

4. The method according to claim 3, wherein the dapansutrile is administered by oral administration.

5. The method according to claim 1, where the method treats melanoma by reducing the size of melanoma.

6. The method according to claim 1, further comprising administering anti-PD-1 antibody to the subject.

* * * * *